(12) United States Patent
Clark (10) Patent No.: US 6,568,935 B2
(45) Date of Patent: May 27, 2003

(54) LINGUAL ARCH DEVELOPER (76) Inventor: William J. Clark, Lundin Lea, Leven Rd, Lundin Links, Fife (GB)

( * ) Notice: Subject to any disclaimer, the term of this patent is extended or adjusted under 35 U.S.C. 154(b) by 0 days.

(21) Appl. No.: 09/842,504

(22) Filed: Apr. 26, 2001

(65) Prior Publication Data

US 2002/0025501 A1 Feb. 28, 2002

Related U.S. Application Data (60) Provisional application No. 60/200,326, filed on Apr. 28, 2000.

(51) Int. Cl.7 ................................................ A61C 7/00
(52) U.S. Cl. ............................................ 433/18; 433/7
(58) Field of Search ............................ 433/18, 17, 19, 433/7, 6, 21

(56) References Cited

U.S. PATENT DOCUMENTS

| | | | |
|---|---|---|---|
| 4,202,100 A | 5/1980 | Forster | 433/7 |
| 4,354,834 A | 10/1982 | Wilson | 433/21 |
| 4,373,913 A | 2/1983 | McAndrew | 433/7 |
| 4,412,819 A | 11/1983 | Cannon | 433/20 |
| 4,573,914 A * | 3/1986 | Nord | 433/18 |
| 4,592,725 A | 6/1986 | Goshgarian | 433/7 |
| 4,723,910 A * | 2/1988 | Keller | 433/7 |
| 5,087,196 A | 2/1992 | Polanco | 433/21 |
| 5,167,499 A | 12/1992 | Arndt et al. | 433/7 |
| 5,399,087 A | 3/1995 | Arndt | 433/7 |
| 5,562,445 A | 10/1996 | DeVincenzo et al. | 433/19 |
| 5,769,631 A * | 6/1998 | Williams | 433/7 |
| 5,785,520 A | 7/1998 | Carano et al. | 433/7 |
| 5,816,800 A | 10/1998 | Brehm et al. | 433/7 |
| 5,829,970 A * | 11/1998 | Yousefian | 433/7 |
| 5,871,350 A | 2/1999 | Clark et al. | 433/18 |
| 6,162,051 A | 12/2000 | Brehm et al. | 433/19 |
| 6,220,856 B1 * | 4/2001 | Carano et al. | 433/7 |
| 6,358,255 B1 * | 3/2002 | Testa | 606/105 |

FOREIGN PATENT DOCUMENTS

| | | |
|---|---|---|
| DE | 27 44 740 A | 4/1979 |
| DE | 39 15 807 A | 11/1990 |
| FR | 1.165.755 | 10/1985 |
| WO | WO 99/59494 | 11/1999 |

* cited by examiner

Primary Examiner—Kevin Shaver
Assistant Examiner—Melba Bumgarner
(74) Attorney, Agent, or Firm—Marsh Fischmann & Breyfogle LLP (57) ABSTRACT Various embodiments of lingual arch developers are disclosed that have at least one telescoping force generator module assemblies for exerting at least generally mesio-distally directed forces on each side of the patient's arch for arch lengthening, as well as at least one telescoping force generator module assembly for exerting at least generally transversely directed forces on the patient's arch for arch expansion.

14 Claims, 5 Drawing Sheets

FIG.9

LINGUAL ARCH DEVELOPER

RELATED APPLICATIONS

This application claims priority from U.S. Provisional Patent Application Serial No. 60/200,326, that was filed on Apr. 28, 2000, and that is entitled "LINGUAL ARCH DEVELOPER."

FIELD OF THE INVENTION

The present invention generally relates to the development of the dental arch of a patient and, more particularly, to a lingual arch developer that utilizes at least one telescoping force generator module on each side of the patient's dental arch to increase a length dimension of the patient's dental arch, as well as at least one telescoping force generator module to increase a width dimension of the patient's dental arch.

BACKGROUND OF THE INVENTION

There are various types of arches in the prior art for applying treatment forces on the lingual of a patient's dental arch to develop or change the shape of this dental arch in at least some manner (generally, "lingual arches"). One way in which the patient's dental arch may be at least generally reshaped is by increasing the length of the dental arch, or its mesio-distal extent. Another way in which the dental arch may be at least generally reshaped is by increasing its width or its lateral extent. Oftentimes the reshaping that is desired by the orthodontist is some combination of both dental arch length and width.

Many different ways of generating the desired treatment forces by lingual arches have been proposed/implemented. Expansion of the patient's dental arch may be accomplished by a resilient, generally U-shaped lingual wire whose two "legs" must be compressed toward each other in order to install the same within the patient's mouth on the lingual. The resiliency of the two legs of the lingual wire exerts a biasing force on the lingual of posterior teeth of the patient's dental arch in a direction that is at least generally transverse to the midline of the patient's dental arch. Another expansion approach is to anchor a wire on opposite sides of the patient's upper dental arch, and to form/include one or more force generating loops in the wire to generate at least generally transversely directed forces (i.e., transverse to the midline of the dental arch). Still another approach is palatal expansion by what is commonly referred to as a palatal expansion screw.

Forces to lengthen the patient's dental arch have also been proposed/implemented by forming/including force generating loops in a resilient lingual wire that is appropriately anchored to this dental arch. Other approaches have utilized compression springs or the like to generate at least generally mesio-distally directed forces for lingual arch development.

There remains need for a lingual arch developer that can generate at least generally mesio-distally directed treatment forces on both sides of the patient's dental arch, as well as expansion forces on the patient's dental arch, preferably without being unnecessarily mechanically complex.

SUMMARY OF THE INVENTION

The present invention generally relates to a lingual arch developer that may be anchored to at least two teeth on opposite sides of a patient's dental arch (i.e., on opposite sides of the midline of the patient's dental arch). Any appropriate way of accomplishing this anchorage may be utilized, including using orthodontic bands and at least generally horizontally disposed tube attached to the bands. The lingual arch developer associated with the present invention is embodied in a configuration that includes at least one telescoping force generator module assembly on each side of the lingual arch developer, namely on each side of the developer's midline, for exerting at least generally mesio-distally directed forces on both sides of the patient's dental arch when this lingual arch developer is installed on the lingual of the patient's dental arch (hereafter "mesio-distal force generator module assemblies"). These types of forces promote a lengthening of the patient's dental arch. The noted lingual arch developer configuration that embodies the present invention also includes at least one telescoping force generator module assembly that is incorporated into the lingual arch developer so as to exert forces on the patient's dental arch that will tend to widen or increase the width of the same (e.g., at least generally transverse to the midline of the patient's dental arch, and thereby a "transverse force generator module assembly").

Various refinements exist of the features noted in relation to the present invention. Further features may also be incorporated in the present invention as well. These refinements and additional features may exist individually or in any combination. The lingual arch developer may be characterized as having a posterior section and an anterior section that are disposed on opposite sides of each of the mesio-distal force generator module assemblies (the posterior section being disposed on the posterior side of the mesio-distal force generator module assembly, and the anterior section being disposed on the anterior side of the mesio-distal force generator module assembly). At least one or both of each anterior section and its corresponding posterior section may be slidably or telescopingly interconnected with its corresponding mesio-distal force generator module assembly. In any case, each anterior section and its corresponding posterior section are biased apart at least generally along a mesio-distal reference axis by their corresponding mesio-distal force generator module assembly.

In one embodiment, the noted anterior sections that may be associated with each of the mesio-distal force generator module assemblies may be part of a one-piece lingual arch. For instance, a first anterior section on a first side of the midline of the lingual arch developer and a second anterior section on a second side of the midline of the lingual arch developer may be of one-piece construction, with each of its two free ends then interfacing with its own mesio-distal force generator module assembly on opposite sides of the patient's dental arch. In another embodiment, the noted anterior sections may be separate structures (e.g., symmetric or asymmetric relative to the midline of the lingual arch developer), having one end that is slidably or telescopingly interconnected with the transverse force generator module assembly (e.g., for the case where the transverse force generator module assembly is disposable at least generally proximate to the tip of the patient's tongue, most typically for a lower dental arch application, and such that the transverse force generator module assembly would bias the first and second anterior sections apart in an at least generally transverse direction relative to the midline of the patient's dental arch), and having an opposite end that is slidably or telescopingly interconnected with its corresponding mesio-distal force generator module assembly. For instance, one portion of each of the noted anterior sections could be disposed so as to interface with at least one of a central and a lateral of the patient's dental arch and the transverse force generator module assembly, while another portion of each of the noted anterior sections could be disposed so as to interface with at least one of a cuspid, a first bicuspid, and a second bicuspid of the patient's dental arch and its corresponding mesio-distal force generator module assembly.

The transverse force generator module assembly may be incorporated into the lingual arch developer by what may be characterized as a transverse wire assembly. Generally, the transverse wire assembly would then extend from one side of the lingual arch developer to its opposite side (i.e., from one side of its midline to the opposite side of its midline). This transverse wire assembly may include or be defined by the noted pair of anterior sections in the case where the transverse force generator module assembly is disposed at least generally proximate to the tip of the patient's tongue. This will typically be the case for when the lingual arch developer is adapted for a lower dental arch application. The transverse wire assembly may also be more distally disposed, such as for an upper dental arch application. In this case, the transverse wire assembly may be shaped so as to extend up toward the palate of the patient.

The mesio-distal force generator module assemblies may be disposed at any appropriate mesio-distal position, including where they are disposed at the same mesio-distal position and at different mesio-distal positions (e.g., symmetric or asymmetric). The treatment forces generated by the mesio-distal force generator module assemblies may also be the same or of different magnitudes. The transverse force generator module assembly may be disposed at any appropriate mesio-distal position as well (although in an orientation to generate at least generally transversely directed expansion forces), and may be symmetrically or asymmetrically disposed relative to the midline of the patient's dental arch on which the lingual arch developer is to be installed. The magnitude of the biasing forces exerted by the transverse force generator module assembly may also be of any appropriate magnitude, including being the same as or different from that provided by the mesio-distal force generator module assemblies.

In the case where the lingual arch developer is adapted for a lower dental arch application, the pair of mesio-distal force generator module assemblies and the transverse force generator module assembly will typically be at least generally coplanar. However, where the lingual arch developer is adapted for an upper dental arch application, although the pair of mesio-distal force generator module assemblies will still likely be disposed in at least generally coplanar relation, the transverse force generator module assembly will typically be vertically offset from the mesio-distal force generator module assemblies so as to be disposed within the vault defined by the patient's palate or at least above the patient's tongue.

DETAILED DESCRIPTION

Figure 1:
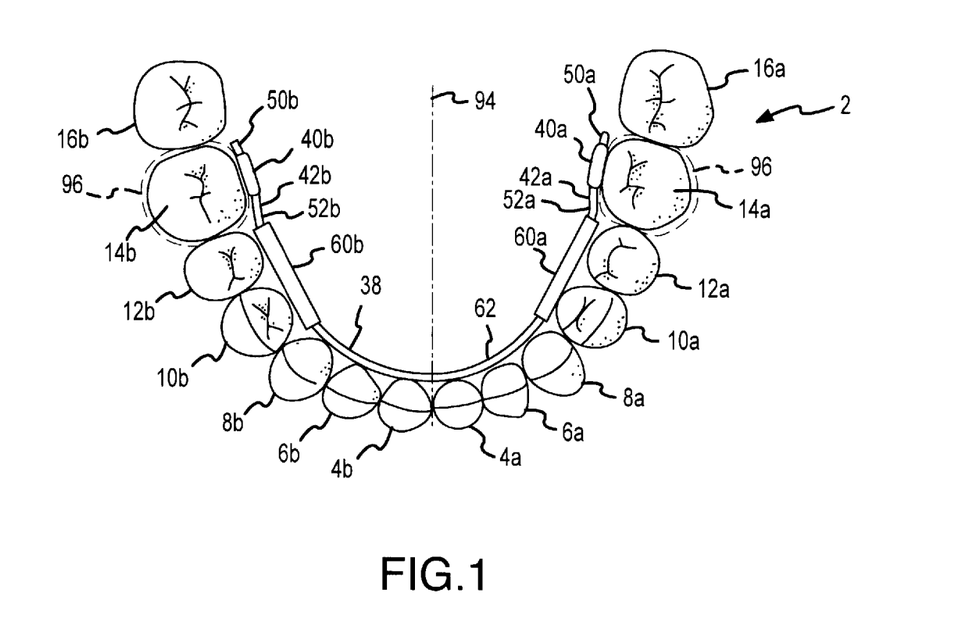
FIG. 1 is a plan view of a lower dental arch of a patient with part of one embodiment of a lingual arch developer installed thereon.

The present invention will be described in relation to the accompanying drawings which at least assist in illustrating the various pertinent features thereof. FIG. 1 illustrates a lower dental arch 2 of a patient. The lower dental arch 2 generally includes the same type of teeth on each side of a midline 94 thereof. Teeth on one side of the midline 94 include an "a" designation, while teeth on the opposite side of the midline 94 include a "b" designation. Each side of the lower dental arch 2 includes the following teeth: a lower central 4, a lower lateral 6, a lower cuspid 8, a lower first bicuspid 10, a lower second bicuspid 12, a lower first molar 14, and a lower second molar 16.

Figure 2:
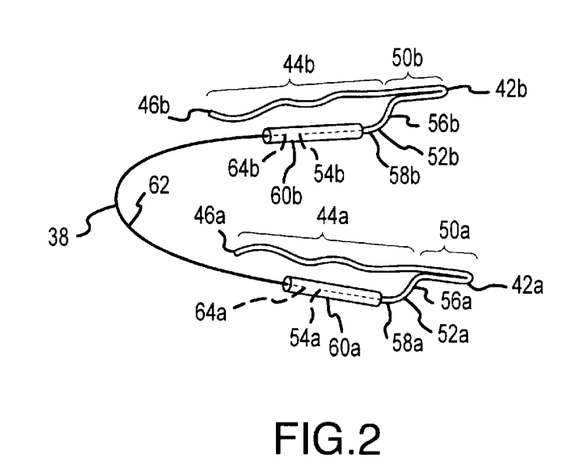
FIG. 2 is a perspective view of the entirety of the lingual arch developer of FIG. 1.

Referring now to both FIGS. 1–2, a lingual arch developer 38 is installed on the lingual side of the lower dental arch 2, and has a midline that corresponds with reference numeral 94. The lingual arch developer 38 is interconnected with the lower dental arch 2 by a pair of at least generally horizontally disposed tubes 40. "Horizontal" in this case means at least generally parallel with the occlusal plane associated with the lower dental arch 2. These tubes 40 are installed on the lower first molars 14 on each side of the midline 94 of the arch 2. Typically these tubes 40 will be brazed onto conventional orthodontic bands 96 which encircle the lower first molars 14. Any appropriate way of interconnecting the lingual arch developer 38 with the lower dental arch 2 may be utilized (e.g., any suitable way of anchoring the developer 38 to a pair of teeth on opposite sides of the midline 94).

The lingual arch developer 38 includes a pair of pre-shaped wires 42 (e.g., posterior sections) which are disposed on opposite sides of the midline 94 of the lower dental arch 2 (i.e., one on the "a" side and one on the "b" side). Only one of these pre-shaped wires 42 will be discussed herein since they are the same, although obviously they are the mirror image of each other in at least some respect. Typical characteristics of the wire 42 are that it should be sufficiently flexible so as to be able to be formed into the shape described herein, but thereafter sufficiently stable so as to at least generally retain this shape and be a supporting framework for the lingual arch developer 38. FIG. 2 illustrates that the wire 42 includes a first mesial extension 44 which terminates at an end 46. This first mesial extension 44 is not illustrated in FIG. 1. A portion of the wire 42 which is disposed distally from the first mesial extension 44 is effectively doubled over onto itself to define an at least generally horizontally disposed post 50 which is disposed within one of the horizontal tubes 40. That is, two at least generally mesio-distally extending sections of the wire 42 are disposed at least substantially adjacent to each other, and more preferably in interfacing relation, to define a corresponding post 50.

Finally, the wire 42 includes a second mesial extension 52 which extends at least generally mesially from its corresponding post 50. A first section 56 of this second mesial extension 52 extends at least gingivally from its corresponding post 50, although it more preferably extends both mesially and gingivally from this post 50. A second section 58 of the second mesial extension 52 extends at least substantially in a mesial direction where the wire 42 terminates at an end 54. Since the first mesial extension 44 is more occlusally disposed than the second mesial extension 52, it would be appropriate to characterize the extension 44 as an occlusal mesial extension 44 of the wire 42 and the extension 52 as a gingival mesial extension 52 of the wire 42. Although the wire 42 has been described as having multiple parts, the wire 42 is in fact an integral structure which is formed from a single piece of material (i.e., no joint of any kind therewithin) into the shape illustrated in FIGS. 1–2.

Another component of the lingual arch developer 38 of FIGS. 1–2 is a lingual arch 62 (e.g., an anterior section) which is disposed mesially of each of the two wires 42 and which interfaces with the lingual surface of anterior teeth within the lower dental arch 2. Disposed between the lingual arch 62 and each of the laterally spaced wires 42 is a force generator module assembly 60. Both force generator module assemblies 60 are only schematically depicted in FIGS. 1–2, and will typically be disposed at least generally at the same elevation or in at least generally coplanar relation. Details of various embodiments which may be utilized by the force generator module assemblies 60 are presented FIGS. 6–7 and 8–9 and will be discussed in more detail below. Suffice it to say for now that the end 54 of each wire 42 extends within its corresponding force generator module assembly 60 and is slidably or telescopingly engaged with a portion thereof Each end 64 of the lingual arch 62 also extends within its corresponding force generator module assembly 60 as well (i.e., the one disposed on the same side of the lower dental arch 2) and is slidably or telescopingly engaged with a portion thereof. At least generally mesially-directed forces are exerted on the lingual arch 62 by both force generator module assemblies 60 as a result of the anchorage provided for the lingual arch developer 38 by the lower first molars 14, and the telescoping interconnection between the lingual arch 62 and each of the two wires 42 which is provided by the two force generator module assemblies 60. These mesially-directed forces in turn are transmitted to those teeth of the lower dental arch 2 which interface with the lingual arch 62 to affect a "lengthening" of the lower dental arch 2 in at least some respect. That is, each second mesial extension 52 and a portion of the lingual arch 62 that extends mesially from the corresponding force generator module assembly 60 are biased apart at least generally along a mesio-distal reference axis or along the mesio-distal extent of the lower dental arch 2.

The force generator module assemblies 60a, 60b may be disposed at the same mesio-distal position as shown in FIGS. 1–2, or may be disposed at different mesio-distal positions (not shown). That is, the second mesial extension 52a and the second mesial extension 52b may be of the same mesio-distal extent or of different mesio-distal extents, and the ends 64a, 64b of the lingual arch 62 may be disposed at the same or different mesio-distal positions. Moreover, the force generator module assemblies 60a, 60b may generate the same or different biasing forces.

Other forces are exerted on the lower dental arch 2 by the lingual arch developer 38. Each of the first mesial extensions 44 may be configured so as to exert forces on the teeth interfacing therewith. Forces applied to the lower dental arch 2 by the extensions 44 are directed at least generally away from the midline 94 of the arch 2. Stated another way, the lingual arch developer 38 may be used to expand the lower dental arch 2 in a direction which is at least generally transverse to the midline 94 of the arch 2. That is, the lingual arch developer 38 exerts forces on the lower dental arch 2 so as to "widen" the same. Typically the first mesial extensions 44 will engage their corresponding lower cuspid 8, lower first bicuspid 10, and lower second bicuspid 12.

Figure 3:
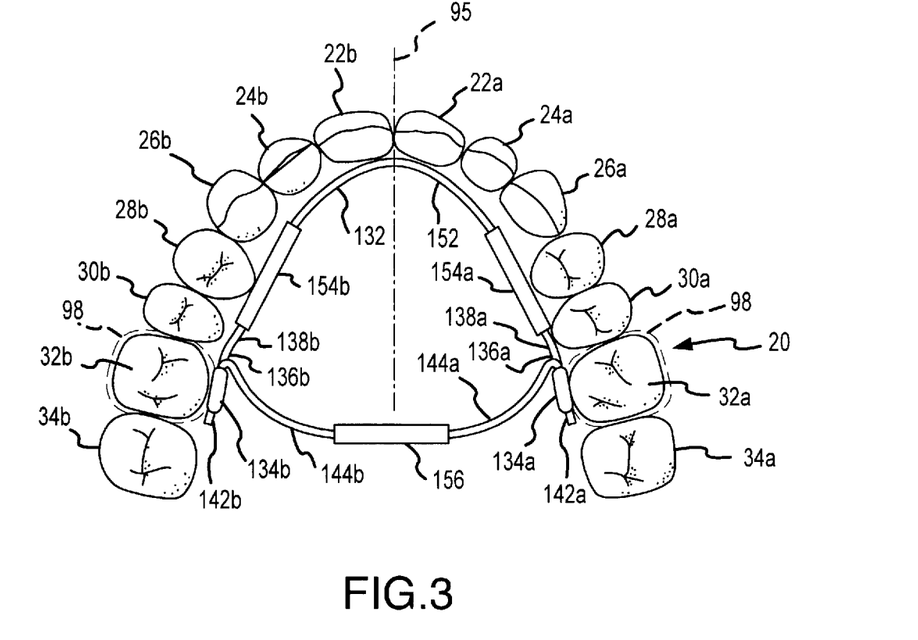
FIG. 3 is a plan view of an upper dental arch of a patient with another embodiment of a lingual arch developer installed thereon.

FIG. 3 illustrates an upper dental arch 20 of a patient. The upper dental arch 20 generally includes the same type of teeth on each side of a midline 95 thereof. Teeth on one side of the midline 95 include an "a" designation, while teeth on the opposite side of the midline 95 include a "b" designation. Each side of the upper dental arch 20 includes the following teeth: an upper central 22, an upper lateral 24, an upper cuspid 26, an upper first bicuspid 28, an upper second bicuspid 30, an upper first molar 32, and an upper second molar 34.

Figure 4:
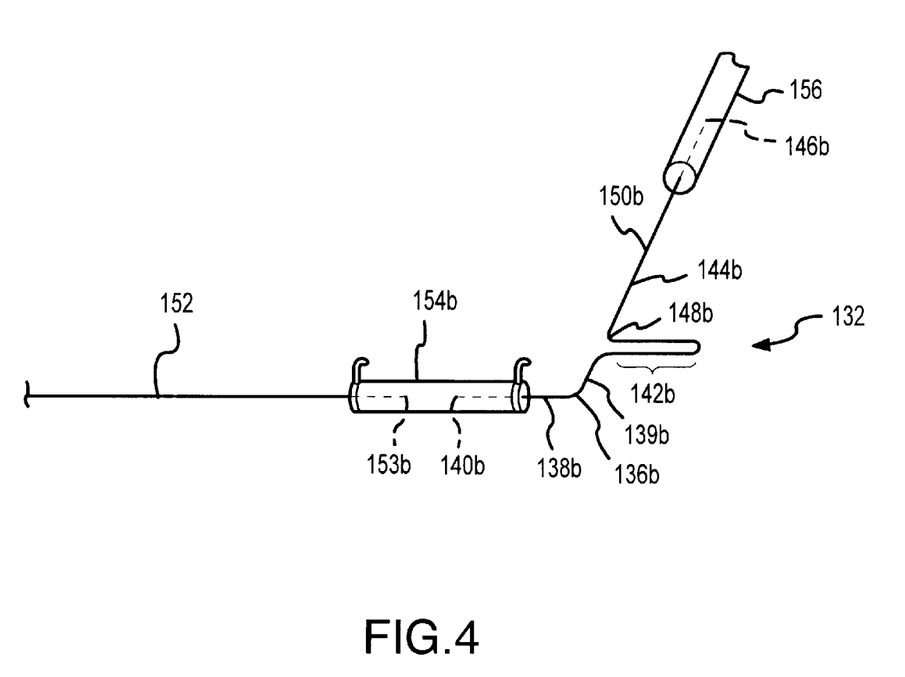
FIG. 4 is a perspective view of part of the lingual arch developer of FIG. 3.

Referring now to both FIGS. 3–4, a lingual arch developer 132 is installed on the lingual side of the upper dental arch 20, and has a midline that corresponds with the reference numeral 95. The lingual arch developer 132 is interconnected with the upper dental arch 20 by a pair of at least generally horizontally disposed tubes 134. "Horizontal" in this case means at least generally parallel with the occlusal plane associated with the upper dental arch 20. These tubes 134 are installed on the upper first molars 32 on each side of the arch 20. Typically these tubes 134 will be brazed onto conventional orthodontic bands 98 which encircle the upper first molars 32. Any appropriate way of interconnecting the lingual arch developer 132 with the upper dental arch 20 may be utilized (e.g., any suitable way of anchoring the developer 132 to a pair of teeth on opposite sides of the midline 95).

The lingual arch developer 132 includes a pair of pre-shaped wires 136 (e.g., posterior sections) which are disposed on opposite sides of the midline 95 upper dental arch 20. Only one of these pre-shaped wires 136 will be discussed since they are the same, although obviously they are the mirror image of each other in at least some respect. Initially, the characteristics noted above with regard to the wires 42 of the lingual arch developer 38 are equally applicable to the wires 136 of the lingual arch developer 132. However, the wires 136 are pre-shaped into a different configuration than the wires 42. In this regard, the wire 136 includes a first mesial extension 138 which terminates at an end 140 of the wire 136. This end 140 is disposed within a force generator module assembly 154 as will be discussed in more detail below. A portion of the wire 136 which is disposed distally from the first mesial extension 138 is effectively doubled over onto itself to define an at least generally horizontally disposed post 142 which is disposed within one of the horizontal tubes 134. That is, two at least generally mesio-distally extending sections of the wire 136 are disposed at least substantially adjacent to each other, and more preferably in interfacing relation, to define a corresponding post 142. A first section 139 of the first mesial extension 138 extends at least occlusally, and more preferably both mesially and occlusally, from its corresponding post 142. The remainder of the first mesial extension 138 extends primarily mesially, and typically in at least substantially horizontal relation (e.g., at least generally parallel with the occlusal plane of the upper dental arch 20).

Finally, the wire 136 includes a palatal extension 144 which extends from a mesial end of its corresponding post 142. A first section 148 of this palatal extension 144 extends occlusally or toward the palate of the patient on which the lingual arch developer 132 is installed, while a second section 150 extends at least generally transversely to the midline of the upper dental arch 20 in at least general proximity to the patient's palette. The wire 136 thereafter terminates at an end 146. This end 146 is disposed within a force generator module assembly 156 which will be discussed in more detail below. Since the first mesial extension 138 is more occlusally disposed than the palatal extension 144, it would be appropriate to characterize the extension 138 as an occlusal mesial extension 138. Although the wire 136 has been described as having multiple parts, the wire 136 is in fact an integral structure which is formed from a single piece of material (i.e., no joint of any kind therewithin) into the shape illustrated in FIGS. 3–4.

Another component of the lingual arch developer 132 of FIGS. 3–4 is a lingual arch 152 (e.g., an anterior section) which is disposed mesially of each of the two wires 136 and which interfaces with the lingual surface of anterior teeth within the upper dental arch 20. Disposed between the lingual arch 152 and each of the laterally spaced wires 136 is a force generator module assembly 154. Both force generator module assemblies 154 are only schematically depicted in FIGS. 3–4 as noted, and will typically be disposed at least generally at the same elevation or in at least generally coplanar relation. Details of various embodiments which may be utilized by the force generator module assembly 154 are presented FIGS. 6–7 and 8–9 and will be discussed in more detail below. Suffice it to say for now that the end 140 of each wire 136 extends within its corresponding force generator module assembly 154 and is slidably or telescopingly engaged with a portion thereof. Each end 153 of the lingual arch 152 also extends within its corresponding force generator module assembly 154 as well (i.e., the one disposed on the same side of the upper dental arch 20). At least generally mesially-directed forces are exerted on the lingual arch 152 by both force generator module assemblies 154 as a result of the anchorage provided for the lingual arch developer 132 by the upper first molars 32, and the telescoping interconnection between the lingual arch 152 and each of the two wires 136 which is provided by the two force generator module assemblies 154. These mesially-directed forces in turn are transmitted to those teeth of the upper dental arch 20 which interface with the lingual arch 152 to affect a "lengthening" of the upper dental arch 20 in at least some respect. That is, each first mesial extension 138 and a portion of the lingual arch 152 that extends mesially from the corresponding force generator module assembly 154 are biased apart at least generally along a mesio distal reference axis or along the mesio-distal extent of the upper dental arch 20.

The force generator module assemblies 154a, 154b may be disposed at the same mesio-distal position as shown in FIG. 3, or may be disposed at different mesio-distal positions (not shown). That is, the first mesial extension 138a and the first mesial extension 138b may be of the same mesio-distal extent or of different mesio-distal extents, and the ends 153a, 153b of the lingual arch 152 may be disposed at the same or different mesio-distal positions. Moreover, the force generator module assemblies 154a, 154b may generate the same or different biasing forces.

Other forces are exerted on the upper dental arch 20 by the lingual arch developer 132. At least one force generator module assembly 156 is disposed between the palatal extensions 144 of the two wires 136 which are again disposed on opposite sides of the midline 95 of the upper dental arch 20 in the illustrated embodiment. As such, the force generator module assembly 156 is disposed at a different elevation than typically both force generator module assemblies 154, and will typically be disposed at least generally adjacent to the palate or roof of the patient's mouth. Details of various embodiments which may be utilized by the force generator module assembly 156 are presented FIGS. 6–7 and 8–9 and will be discussed in more detail below. Suffice it to say for now that the end 146 of each wire 136 extends within the force generator module assembly 156 and is slidably or telescopingly engaged with a portion thereof. At least generally transversely directed forces are exerted on at least some of the teeth within the upper dental arch 20 which interface in at least some respect with the lingual arch developer 132 as a result of the telescoping interconnection between the two wires 136 (more specifically their respective palatal extensions 144) which is provided by the force generator module assembly 156. That is, the lingual arch developer 132 exerts forces on the upper dental arch 20 so as to "widen" the same or so as to bias the palatal extensions 144 apart in an at least generally transverse direction relative to the midline 95.

The force generator module assembly 156 may be symmetrically disposed relative to the midline 95 (i.e., such that the palatal extensions 144 are the same length) as illustrated in FIG. 3, or may be asymmetric relative to the midline 95 (not shown, but such that the palatal extensions 144a, 144b would be of different lengths, including the situation where the ends 146a, 146b of the extensions 144a, 144b are both disposed on the same side of the midline 95). The force generator module assembly 156 also may generate biasing forces that are the same or different from those biasing forced generated by the force generator module assemblies 154.

Figure 5:
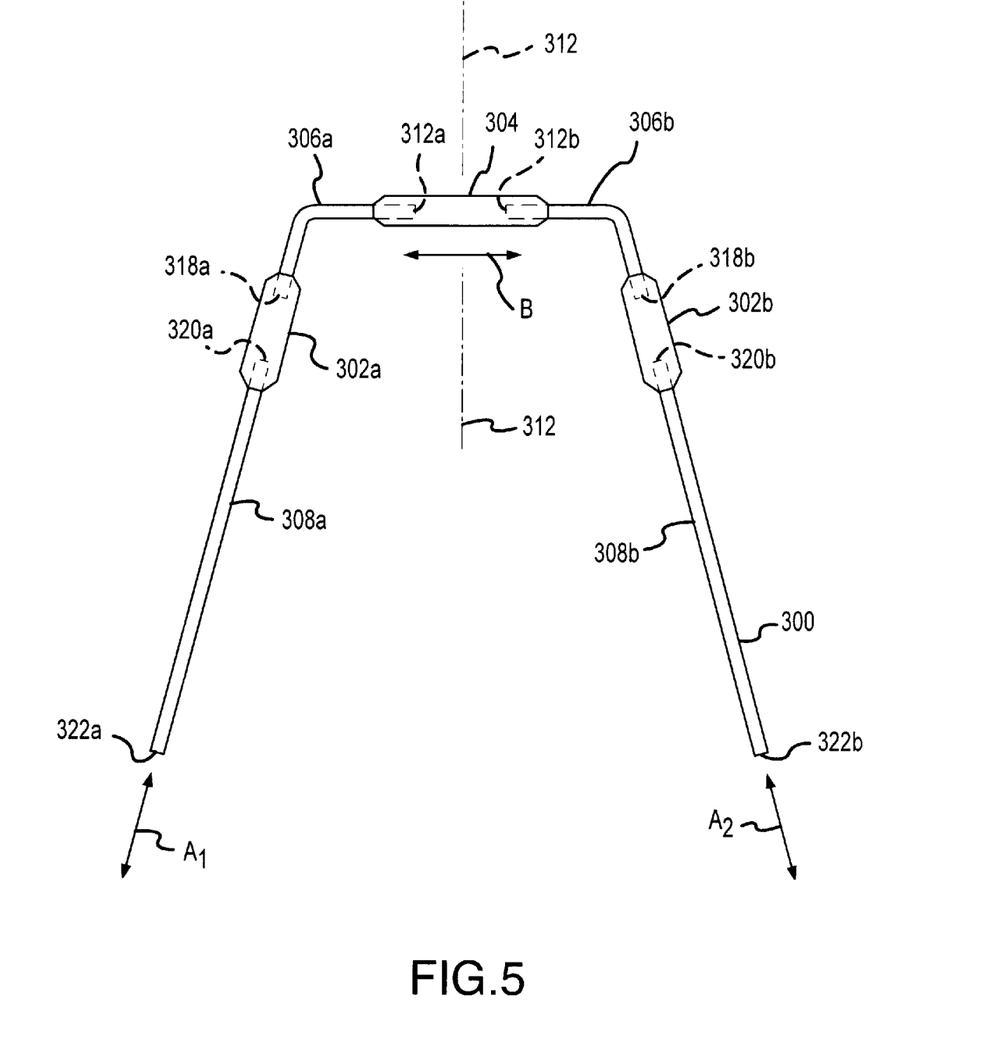
FIG. 5 is a plan view of another embodiment of a lingual arch developer.

Another embodiment of a lingual arch developer is presented in FIG. 5. The lingual arch developer 300 is for the lower dental arch 2 of the patient and would assume the same general position as the lingual arch developer 38 illustrated in FIG. 1. The lingual arch developer 300 generally includes what may be characterized as a pair of anterior sections 306a, 306b, a pair of posterior sections 308a, 308, a pair of mesio-distal force generator module assemblies 302a, 302b, and a transverse force generator module assembly 304. Typically, the transverse force generator module assembly 304 and both mesio-distal force generator module assemblies 302a, 302b will be disposed at least at generally the same elevation or in at least generally coplanar relation. Details of various embodiments which may be utilized by the force generator module assemblies 302, 304 are presented FIGS. 6–7 and 8–9 and will be discussed in more detail below.

One end 312a, 312b of each of the anterior sections 306a, 306b interfaces with the transverse force generator module assembly 304, while the opposite ends 318a, 318b of these anterior sections 306a, 306b interface with the mesio-distal force generator module assembly 302a, 302b, respectively. One of the ends 320a, 320b of each of the posterior sections 308a, 308b interface with the mesio-distal force generator module assemblies 302a, 302b, while the opposite ends 322a, 322b of the posterior sections 308a, 308b will extend within/through the types of horizontal tubes 40 illustrated in FIG. 1 to secure or anchor the lingual arch developer 300 to the lower dental arch 2 of the patient. Any appropriate way of anchoring the posterior sections 308a, 308b, to the upper dental arch 20 may be utilized.

The transverse force generator module assembly 304 is disposed at least generally proximate to the tip of the patient's tongue, typically slightly mesially thereof and/or possibly slightly below the tongue. It should be appreciated that the transverse force generator module assembly 304 need not be symmetrically disposed relative to the midline 312 of the developer 300, but instead may be disposed more on one side of the lower dental arch 2 than the other. That is, the ends 312a, 312b of the anterior sections 306a, 306b may be disposed at the same position relative to the midline 312 as shown in FIG. 5, or may be disposed at different positions relative to the midline 312 (not shown, but including the situation where the ends 312a, 312b are both actually disposed on the same side of the midline 312).

At least one of, and possibly both of, the anterior sections 306a, 306b, are slidably or telescopingly interconnected with the transverse force generator module assembly 304. Generally, the transverse force generator module assembly 304 exerts a biasing force on the lingual side of the lower dental arch 2 in a direction so as to expand or increase the width of the lower dental arch 2. Therefore, the transverse force generator module assembly 302 biases the anterior sections 306a, 306b at least generally away from each other along an axis that is at least generally perpendicular to a mesio-distal direction or to the midline 312, or in the direction of the arrow "B" presented in FIG. 5.

The force generator module assembly 302a is slidably or telescopingly interconnected with at least one of, and possibly both of, the anterior section 306a and the posterior section 308a, while the force generator module assembly 302b is slidably or telescopingly interconnected with at least one of, and possibly both of, the anterior section 306b and the posterior section 308b. Generally, each mesio-distal force generator module assembly 302 exerts a biasing force on the lingual of the lower dental arch 2 in a direction so as to lengthen the lower dental arch 2 or increase its mesio-distal extent (i.e., the forces are at least generally mesio-distally directed). Therefore, the mesio-distal force generator module assembly 302a biases the anterior section 306a and posterior section 308a at least generally away from each other along an axis that is at least generally mesially-distally directed or in the direction of the arrow $A_1$, while the mesio-distal force generator module assembly 302b biases the anterior section 306b and posterior section 308b at least generally away from each other along an axis that is at least generally mesially-distally directed or in the direction of the arrow $A_2$. It should be appreciated that the force generator module assemblies 302a, 302b may be disposed at any appropriate mesio-distal location, and need not be disposed at the same mesio-distal position. That is, the ends 318a, 318b of the anterior sections 306a, 306b may be disposed at the same or different mesio-distal positions, while the ends 320a, 320b of the posterior sections 308a, 308b may be disposed at the same or different mesio-distal positions.

Figure 6:
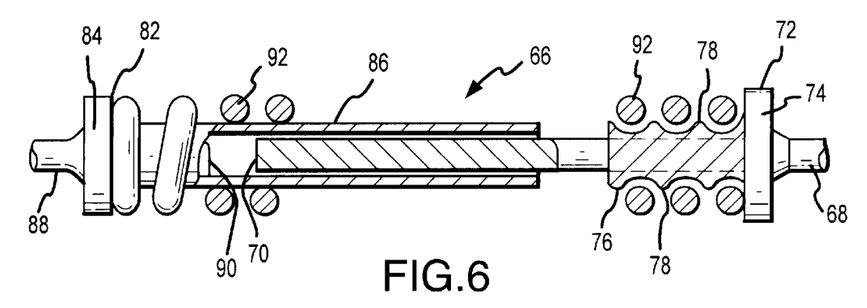
FIG. 6 is a cross-sectional view of one embodiment of a force generator module assembly which may be utilized by either of the lingual arch developers of FIGS. 1, 3, and 5.

One embodiment of a force generator module assembly which may be utilized by each of the lingual arch developer 38 of FIGS. 1–2 (for one or both of the force generator module assemblies 60), the lingual arch developer 132 of FIGS. 3–4 (for one or more of the force generator module assemblies 154 and the force generator module assembly 156), the lingual arch developer 300 of FIG. 5 (for one or more of the force generator module assemblies 302 and the force generator module assembly 304) is illustrated in FIG. 6. The force generator module assembly 66 of FIG. 6 includes a stop 72. This stop 72 includes a bore which extends entirely therethrough. The stop 72 also includes a head or flange 74 and a body 76 with longitudinally spaced, annular barbs or protrusions 78 disposed thereon. Both the flange 74 and body 76 are at least generally cylindrical in one embodiment, with the diameter of the flange 74 being larger than the diameter of the body 76. In any case, a first wire 68 (e.g., the second mesial extension 52 of the lingual arch developer 38, the first mesial extension 138 of the lingual arch developer 132, the palatal extension 144 of the lingual arch developer 132, the lingual arch 62, the lingual arch 152, the anterior section 306, the posterior section 308) extends entirely through the bore within the stop 72 and is appropriately secured to the stop 72 (e.g., via brazing or welding).

Another component of the force generator module assembly 66 is a tube 82. This tube 82 includes a bore which extends entirely therethrough. The tube 82 also includes a head or flange 84 and a body 86 which are preferably integrally formed (i.e., formed from a single piece of material with no joint therebetween). Both the flange 84 and body 86 are at least generally cylindrical in one embodiment, with the diameter of the flange 84 being larger than the diameter of the body 86. In any case, a second wire 88 (e.g., the second mesial extension 52 of the lingual arch developer 38, the first mesial extension 138 of the lingual arch developer 132, the palatal extension 144 of the lingual arch developer 132, the lingual arch 62, the lingual arch 152, the anterior section 306, the posterior section 308) extends within the bore of the tube 82. The first wire 68 also extends within the bore of the tube 82, but from the opposite direction compared to the second wire 88. An end 70 of the first wire 68 and an end 90 of the second wire 88 are disposed in spaced relation within the body 86 of the tube 82.

The stop 72 and tube 82 are biased at least generally away from each other along an at least substantially axial path by a coil spring 92 which is disposed between and abuts each of the flange 74 of the stop 72 and the flange 84 of the tube 82, and which is in an axially compressive state at least at the start of treatment. The coil spring 92 is thereby disposed about the body 76 of the stop 72 and is retained in position thereon by having individual coils being disposed within the spacing between the barbs 78, and is also disposed about the body 86 of the tube 82. The first wire 68 and the second wire 88 are slidably interconnected by the first wire 68 being fixed to the stop 72, by the second wire 88 being fixed to the tube 82, and by the first wire 68 being slidably disposed within the tube 82. Biasing forces provided by the coil spring 92 will increase the distance between the flange 74 of the stop 72 and the flange 84 of the tube 82 by the first wire 68 sliding within the bore of the tube 82 in a direction which is at least generally away from the second wire 88. Therefore, the spacing between the end 70 of the first wire 68 and the end 90 of the second wire 88 will be increased by the action of the spring 92. Again, each of the lingual arch developers 38, 132 noted above may utilize the configuration of the force generator module assembly 66 to increase the spacing between wires/lingual arches which are interconnected by such a force generator module assembly 66.

Figure 7:
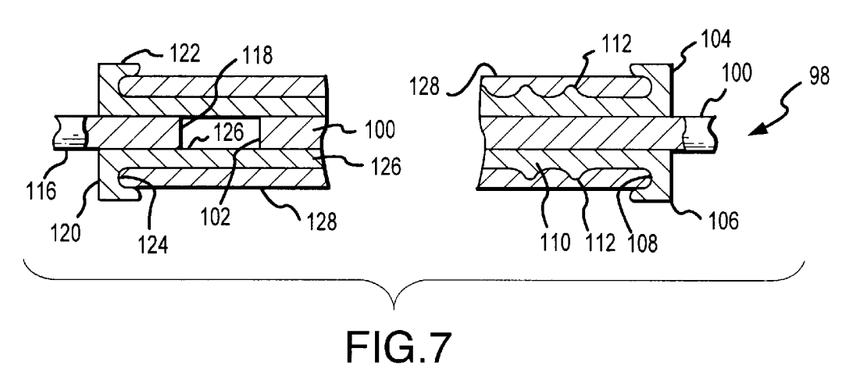
FIG. 7 is a cross-sectional view of another embodiment of a force generator module assembly which may be utilized by either of the lingual arch developers of FIGS. 1, 3, and 5.

Another embodiment of a force generator module assembly which may be utilized by each of the lingual arch developer 38 of FIGS. 1–2 (for one or both of the force generator module assemblies 60), the lingual arch developer 132 of FIGS. 3–4 (for one or more of the force generator module assemblies 154 and the force generator module assembly 156), and the lingual arch developer 300 of FIG. 5 (for one or more of the force generator module assemblies 302 and the force generator module assembly 304) is illustrated in FIG. 7. The force generator module assembly 98 of FIG. 7 includes a stop 104. This stop 104 includes a bore which extends entirely therethrough. The stop 104 also includes a head or flange 106 with an annular groove or seat 108 formed therein, as well as a body 110 with longitudinally spaced, annular barbs or protrusions 112 disposed thereon. Both the flange 106 and the body 110 are at least generally cylindrical in one embodiment, with the diameter of the flange 106 being larger than the diameter of the body 110. In any case, a first wire 100 (e.g., the second mesial extension 52 of the lingual arch developer 38, the first mesial extension 138 of the lingual arch developer 132, the palatal extension 144 of the lingual arch developer 132, the lingual arch 62, the lingual arch 152, the anterior section 306, the posterior section 308) extends entirely through the bore within stop 104 and is appropriately secured to the stop 104 (e.g., via brazing or welding).

Another component of the force generator module assembly 98 is a tube 120. This tube 120 includes a bore which extends entirely therethrough. The tube 120 also includes a head or flange 122 and a body 126 which are preferably integrally formed (i.e., formed from a single piece of material with no joint therebetween). Both the flange 122 and body 126 are at least generally cylindrical in one embodiment, with the diameter of the flange 122 being larger than the diameter of the body 126. In any case, a second wire 116 (e.g., the second mesial extension 52 of the lingual arch developer 38, the first mesial extension 138 of the lingual arch developer 132, the palatal extension 144 of the lingual arch developer 132, the lingual arch 62, the lingual arch 152, the anterior section 306, the posterior section 308) extends within the bore of the tube 120. The first wire 100 also extends within the bore of the tube 120, but from the opposite direction compared to the second wire 116. An end 102 of the first wire 100 and an end 118 of the second wire 116 are disposed in spaced relation within the body 126 of the tube 120.

The stop 104 and tube 120 are biased at least generally away from each other along an at least substantially axial path by an elastomeric tube 128 (e.g., silicon tubing) which is disposed between and abuts each of the flange 106 of the stop 104 and the flange 122 of the tube 120, and which is in an axially compressive state at least at the start of treatment. The elastomeric tube 128 is thereby disposed about the body 110 of the stop 104 and the body 126 of the tube 120. The elastomeric tube 128 is retained in position by being seated within an annular groove 108 formed on a face of the flange 106 of the stop 104, and by being seated within an annular groove 124 formed on a face of the flange 122 of the tube 120. The first wire 100 and the second wire 116 are slidably interconnected by the first wire 100 being fixed to the stop 104, by the second wire 116 being fixed to the tube 120, and by the first wire 100 being slidably disposed within the tube 120. Biasing forces provided by the elastomeric tube 128 will increase the distance between the flange 106 of the stop 104 and the flange 122 of the tube 120 by the first wire 100 sliding within the bore of the tube 120 in a direction which is at least generally away from the second wire 116. Therefore, the spacing between the end 102 of the first wire 100 and the end 118 of the second wire 116 will be increased by the action of the elastomeric tube 128. Again, each of the lingual arch developers 38, 132 noted above may utilize the configuration of the force generator module assembly 98 to increase the spacing between wires/lingual arches which are interconnected by such a force generator module assembly 98.

Figure 8:
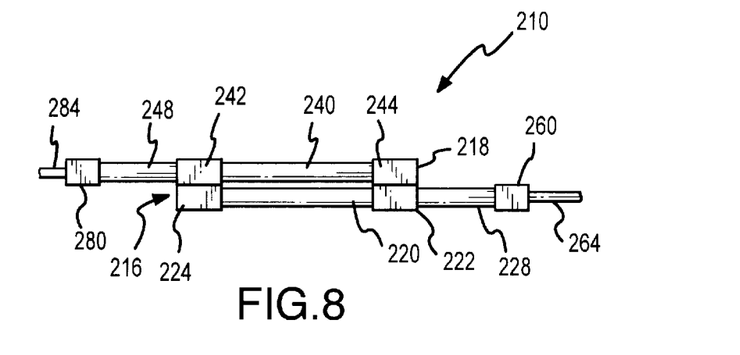
FIG. 8 is a side view of another embodiment of a force generator module assembly which may be utilized by either of the lingual arch developers of FIGS. 1, 3, and 5.
Figure 9:
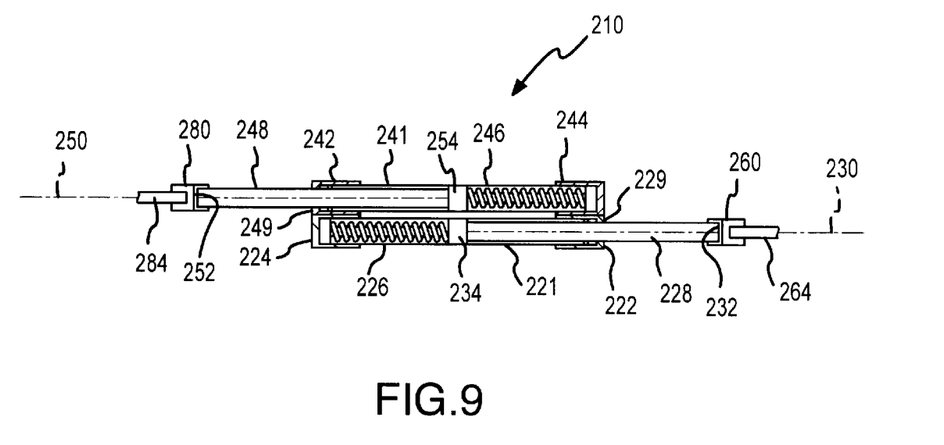
FIG. 9 is a cutaway view of the force generator module assembly of FIG. 8.

Another embodiment of a force generator module assembly which may be utilized by each of the lingual arch developer 38 of FIGS. 1–2 (for one or both of the force generator module assemblies 60), the lingual arch developer 132 of FIGS. 3–4 (for one or more of the force generator module assemblies 154 and the force generator module assembly 156), and the lingual arch developer 300 of FIG. 5 (for one or more of the force generator module assemblies 302 and the force generator module assembly 304) is illustrated in FIGS. 8–9. The force generator module assembly 210 employs dual acting pistons 216, 218 that are interconnected together in tandem. The dual acting piston includes a first piston cylinder 220 having a housing 221 with a first end 222, and a second end 224, with a first compression spring 226 disposed in the first piston cylinder 220. Connected to the first compression spring 226 is a first piston connecting rod 228 extending from a slot 229 in the first end 222 of the first piston cylinder 220, the first piston connecting rod 228 having a longitudinal axis 230, an exterior end 232, and an interior end 234. The interior end 234 of the first piston connecting rod 228 is connected to the first compression spring 226, and is slidable within the piston cylinder housing 221 relative to the first piston cylinder 220 along the longitudinal axis 230 of the first piston connecting rod 228.

The dual acting piston 218 includes a second piston cylinder 240 having a housing 241 with a first end 242 and a second end 244, with a second compression spring 246 disposed in the second piston cylinder 240. A second piston connecting rod 248 is connected to the second compression spring 246, and extends from a slot 249 in the first end 242 of the second piston cylinder 240, the second piston connecting rod 248 having a longitudinal axis 250, an exterior end 252, and an interior end 254. The interior end 254 of the second piston connecting rod 248 is connected to the second compression spring 246, and the second piston connecting rod 248 is slidable within the second piston cylinder housing 241 along the longitudinal axis 250 of the second piston connecting rod 248.

The second piston cylinder 240 is preferably connected adjacent to the first piston cylinder 220, with the first end 222 of the first piston cylinder 220 adjacent to the second end 244 of the second piston cylinder 240, and the second end 224 of the first piston cylinder 220 adjacent to the first end 242 of the second piston cylinder 240, with the exterior ends 232, 252 of the first and second piston connecting rods 228, 248 extending in opposing directions. Alternatively, the first and second piston cylinders 220, 240 can be connected end-to-end (not shown). In a presently preferred embodiment, the first compression spring 226 biases the first piston connecting rod 228 to extend away from the first compression spring 226, and the second compression spring 246 biases the second piston connecting rod 248 to extend away from the second compression spring 246, to bias the first and second connecting rods 228, 248 apart.

The exterior end 232 of the first piston connecting rod 228 extends through one end of a first adapter 260 and is appropriately attached (e.g., welding, brazing) to the first adapter 260. A wire 264 (e.g., the second mesial extension 52 of the lingual arch developer 38, the first mesial extension 138 of the lingual arch developer 132, the palatal extension 144 of the lingual arch developer 132, the lingual arch 62, the lingual arch 152, the anterior section 306, the posterior section 308) extends through the opposite end of the first adapter 260 and is also appropriately attached (e.g., welding, brazing) to the first adapter 260. Similarly, the exterior end 252 of the second piston connecting rod 248 extends through one end of a second adapter 280 and is appropriately attached (e.g., welding, brazing) to the second adapter 280. A wire 284 (e.g., the second mesial extension 52 of the lingual arch developer 38, the first mesial extension 138 of the lingual arch developer 132, the palatal extension 144 of the lingual arch developer 132, the lingual arch 62, the lingual arch 152, the anterior section 306, the posterior section 308) extends through the opposite end of the second adapter 280 and is also appropriately attached (e.g., welding, brazing) to the second adapter 280. Therefore, both sires 264, 284 are slidably or telescopingly interconnected with the force generator module assembly 210.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A lingual arch developer, comprising:
   a midline;
   first and second sides that extend away from said midline in opposite directions;
   first and second anterior sections disposable on a lingual surface on opposite sides of a patient's dental arch;
   first and second posterior sections disposable on the lingual surface on opposite sides of the patient's dental arch;
   first and second means for interconnecting said first and second posterior sections, respectively, with first and second teeth, respectively, disposed on opposite sides of the patient's dental arch;
   first means for slidably interconnecting said first anterior section and said first posterior section;
   first means for biasing said first anterior section and said first posterior section at least generally apart at least generally along a mesio-distal reference axis;
   second means for slidably interconnecting said second anterior section and second posterior section;
   second means for biasing said second anterior section and said second posterior section apart at least generally along a mesio-distal reference axis;
   a transverse wire assembly extending from said first side of said lingual arch developer to said second side of said lingual arch developer at least generally transverse to a first reference axis that extends through said midline to bisect said lingual arch developer, said transverse wire assembly comprising first and second transverse wire sections;
   third means for slidably interconnecting first and second transverse wire sections;
   third means for biasing said first and second transverse wire sections apart at least generally transverse to said first reference axis;
   a first force generator module assembly, wherein said first force generator module assembly comprises said first means for slidably interconnecting and said first means for biasing;
   a second force generator module assembly, wherein said second force generator module assembly comprises said second means for slidably interconnecting and said second means for biasing; and
   a third force generator module assembly, wherein said third force generator module assembly comprises said third means for slidably interconnecting and said third means for biasing, wherein said third force generator module assembly is disposed at a different elevation than each of said first and second force generator module assemblies, and wherein said third force generator module assembly is disposable at least generally proximate to a palate of the patient when said lingual arch developer is installed on the patient's dental arch, wherein said lingual arch developer is adapted for an upper dental arch of the patient.

2. A lingual arch developer, as claimed in claim 1, further comprising:
   a lingual arch, wherein said lingual arch is of one-piece construction, comprises said first and second anterior sections, and is at least generally arcuate.

3. A lingual arch developer, as claimed in claim 1, wherein:
   said first and second anterior sections are symmetrical and a mirror image of each other.

4. A lingual arch developer, as claimed in claim 1, wherein:
   said first and second means for interconnecting each comprises a band and an at least generally horizontal tube attached to said band so as to be disposed on the lingual of the patient's dental arch when said lingual arch developer is installed on the patient's dental arch.

5. A lingual arch developer, as claimed in claim 1, wherein:
   said first and second force generator module assemblies comprise means for increasing a length dimension of the patient's dental arch when said lingual arch developer is installed on the patient's dental arch, and wherein said third force generator module assembly comprises means for increasing a width dimension of the patient's dental arch when said lingual arch developer is installed on the patient's dental arch.

6. A lingual arch developer, as claimed in claim 1, wherein:
   said first and second force generator module assemblies are symmetrically disposed relative to said midline.

7. A lingual arch developer, as claimed in claim 1, wherein:
   said third force generator module assembly is symmetrically disposed relative to said midline.

8. A lingual arch developer, as claimed in claim 1, wherein:
   said transverse wire assembly extends at least generally toward the palate of the patient when said lingual arch developer is installed on the patient's dental arch, wherein said lingual arch developer is adapted for an upper dental arch of the patient.

9. A lingual arch developer, as claimed in claim 1, wherein:
   said transverse wire assembly extends out-of-plane from a reference plane that contains said first and second posterior sections.

10. A lingual arch developer, as claimed in claim 1, wherein:
    said first anterior section and said first transverse wire section are of one-piece construction, and wherein said second anterior section and said second transverse wire section are of one-piece construction.

11. A lingual arch developer, as claimed in claim 1, wherein:
    said patient's dental arch comprises a central, a lateral, a cuspid, a first bicuspid, and a second bicuspid on each side of a patient's midline of the patient's dental arch, wherein when said lingual arch developer is installed on the patient's dental arch: 1) said first transverse wire section is positioned so as to interface with at least one of the central and the lateral on a first side of the patient's midline; 2) said first anterior section is positioned so as to interface with at least one of the cuspid, the first bicuspid, and the second bicuspid on the first side of the patient's midline; 3) said second transverse wire section is positioned so as to interface with at least one of the central and the lateral on a second side of the patient's midline; and 4) said second anterior section is positioned so as to interface with at least one of the cuspid, the first bicuspid, and the second bicuspid on the second side of the patient's midline.

12. A lingual arch developer, as claimed in claim 1, wherein:

said first transverse wire section and said first posterior section merge into an at least generally horizontally disposed first post, wherein said first means for interconnecting comprises an at least generally horizontal first tube that is interconnectable with a first tooth of the patient's dental arch, wherein said first post is disposable within said first tube, wherein said second transverse wire section and said second posterior section merge into an at least generally horizontally disposed second post, wherein said second means for interconnecting comprises an at least generally horizontal second tube that is interconnectable with a second tooth of the patient's dental arch, and wherein said second post is disposable within said second tube.

13. A lingual arch developer, comprising:

a midline;

first and second sides that extend away from said midline in opposite directions;

first and second anterior sections disposable on a lingual surface on opposite sides of a patient's dental arch;

first and second posterior sections disposable on the lingual surface on opposite sides of the patient's dental arch;

first and second means for interconnecting said first and second posterior sections, respectively, with first and second teeth, respectively, disposed on opposite sides of the patient's dental arch;

first means for slidably interconnecting said first anterior section and said first posterior section;

first means for biasing said first anterior section and said first posterior section at least generally apart at least generally along a mesio-distal reference axis;

second means for slidably interconnecting said second anterior section and second posterior section;

second means for biasing said second anterior section and said second posterior section apart at least generally along a mesio-distal reference axis;

a transverse wire assembly extending from said first side of said lingual arch developer to said second side of said lingual arch developer at least generally transverse to a first reference axis that extends through said midline to bisect said lingual arch developer, said transverse wire assembly comprising first and second transverse wire sections;

third means for slidably interconnecting first and second transverse wire sections; third means for biasing said first and second transverse wire sections apart at least generally transverse to said first reference axis;

a first force generator module assembly, wherein said first force generator module assembly comprises said first means for slidably interconnecting and said first means for biasing, wherein said first means for biasing is mounted on a barbed section of said first force generator module assembly;

a second force generator module assembly, wherein said second force generator module assembly comprises said second means for slidably interconnecting and said second means for biasing section, wherein said second means for biasing is mounted on a barbed section of said second force generator module assembly; and a third force generator module assembly, wherein said third force generator module assembly comprises said third means for slidably interconnecting and said third means for biasing, wherein said third means for biasing is mounted on a barbed section of said third force generator module assembly.

14. A lingual arch developer, comprising:

a midline;

first and second sides that extend away from said midline in opposite directions;

first and second anterior sections disposable on a lingual surface on opposite sides of a patient's dental arch;

first and second posterior sections disposable on the lingual surface on opposite sides of the patient's dental arch;

first and second means for interconnecting said first and second posterior sections, respectively, with first and second teeth, respectively, disposed on opposite sides of the patient's dental arch;

first means for slidably interconnecting said first anterior section and said first posterior section;

first means for biasing said first anterior section and said first posterior section at least generally apart at least generally along a mesio-distal reference axis;

second means for slidably interconnecting said second anterior section and second posterior section;

second means for biasing said second anterior section and said second posterior section apart at least generally along a mesio-distal reference axis;

a transverse wire assembly extending from said first side of said lingual arch developer to said second side of said lingual arch developer at least generally transverse to a first reference axis that extends through said midline to bisect said lingual arch developer, said transverse wire assembly comprising first and second transverse wire sections;

third means for slidably interconnecting first and second transverse wire sections; and third means for biasing said first and second transverse wire sections apart at least generally transverse to said first reference axis, wherein said first transverse wire section and said first posterior section merge into an at least generally horizontally disposed first post that is collectively defined by doubling over a portion of said first transverse wire section onto a portion of said first posterior section, wherein said first means for interconnecting comprises an at least generally horizontal first tube that is interconnectable with a first tooth of the patient's dental arch, wherein said first post is disposable within said first tube, wherein said second transverse wire section and said second posterior section merge into an at least generally horizontally disposed second post that is collectively defined by doubling over a portion of said second transverse wire section onto a portion of said second posterior section, wherein said second means for interconnecting comprises an at least generally horizontal second tube that is interconnectable with a second tooth of the patient's dental arch, and wherein said second post is disposable within said second tube.

* * * * *